United States Patent
Boss et al.

(10) Patent No.: US 6,614,523 B1
(45) Date of Patent: *Sep. 2, 2003

(54) SENSOR FOR PERFORMING SURFACE ENHANCED RAMAN SPECTROSCOPY

(75) Inventors: Pamela A. Boss, San Diego, CA (US); Stephen H. Lieberman, La Mesa, CA (US); Leonard J. Martini, San Diego, CA (US); Leon V. Smith, San Diego, CA (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 163 days.

This patent is subject to a terminal disclaimer.

(21) Appl. No.: 09/805,665

(22) Filed: Mar. 13, 2001

Related U.S. Application Data

(63) Continuation-in-part of application No. 09/593,675, filed on Jun. 14, 2000, now Pat. No. 6,406,777.

(51) Int. Cl.[7] .................................................. G01J 3/44
(52) U.S. Cl. ...................................................... 356/301
(58) Field of Search ................................ 356/301, 300; 600/310, 314, 315–323

(56) References Cited

U.S. PATENT DOCUMENTS

| | | | |
|---|---|---|---|
| 4,781,458 A | * | 11/1988 | Angel et al. ................. 356/301 |
| 5,010,776 A | | 4/1991 | Lucero et al. |
| 5,112,127 A | | 5/1992 | Carrabba et al. |
| 5,194,913 A | | 3/1993 | Myrick et al. |
| 5,241,368 A | | 8/1993 | Ponstingl et al. |
| 5,376,556 A | | 12/1994 | Tarcha et al. |
| 5,402,508 A | | 3/1995 | O'Rourke et al. |
| 5,739,536 A | | 4/1998 | Bucholtz et al. |
| 5,759,859 A | | 6/1998 | Sausa |
| 5,774,610 A | | 6/1998 | O'Rourke et al. |
| 5,864,397 A | * | 1/1999 | Vo-Dinh ..................... 356/301 |
| 6,018,389 A | | 1/2000 | Kyle et al. |
| 6,028,666 A | | 2/2000 | Boss et al. |
| 6,406,777 B1 | * | 6/2002 | Boss et al. .................. 428/209 |

OTHER PUBLICATIONS

Storey, J. M. E. et al., "Electrochemical SERS Detection of Chlorinated Hydrocarbons in Aqueous Solutions", *Applied Spectroscopy*, vol. 48, No. 10, 1994.

Mullen, K. et al., "Adsorption of Chlorinated Ethylenes at 1–Octadecanethiol–Modified Silver Surfaces", *Analytical Chemistry*, vol. 66, No. 4, Feb. 15, 1994.

Schoen, C. L. et al., "Long fiber–optic remote Ramen probe for detection and identification of weak scatterers", *Applied Optics*, vol. 31, No. 36, Dec. 20, 1992.

(List continued on next page.)

*Primary Examiner*—Tu T. Nguyen
(74) *Attorney, Agent, or Firm*—Michael A. Kagan; Peter A. Lipovsky; Allan Y. Lee

(57) ABSTRACT

A sensor for performing surface enhanced Raman spectroscopy (SERS) includes a sensor body having a throughbore; a window mounted to the sensor body that is coterminous with the throughbore; surface enhanced Raman scattering structure mounted to the window; an optical energy source for generating an optical excitation signal; a first optical fiber mounted in the throughbore for directing the optical excitation signal through the surface enhanced Raman scattering (SERS) structure; a second optical fiber mounted in the throughbore for receiving primary Raman emissions generated when an analyte in contact with the surface enhanced Raman scattering structure is irradiated by the optical excitation signal; and an optical detector for generating an optical signal representing the primary Raman emissions.

13 Claims, 5 Drawing Sheets

OTHER PUBLICATIONS

Crane, L. G. et al., "SERS Surfaces Modified with a 4–(2–Pyridylazo) resorcinol Disulfide Derivative: Detection of Copper, Lead, and Cadmium", *Analytical Chemistry*, vol. 67, No. 2, Jan. 15, 1995.

Carron, K. T. et al., "Molecular–Specific Chromatographic Detector Using MOdified SERS Substrates", *Analytical Chemistry*, vol. 67, No. 18, Sep. 15, 1995.

Carron, K. et al., "Octadecylthiol–Modified Surface–Enhanced Raman Spectroscopy Substrates: A New Method for the Detection of Aromatic Compounds", Environ. Sci. Technol., vol. 26, No. 10, 1992.

Carrabba, M. M. et al., "Fiber Optic Raman Chemical Sensors", *Proceedings of the Sumposium on Chemical Sensors II*, vol. 93–7.

* cited by examiner

SENSOR FOR PERFORMING SURFACE ENHANCED RAMAN SPECTROSCOPY

CROSS REFERENCE TO RELATED APPLICATIONS

This application is a continuation-in-part of commonly assigned U.S. patent application Ser. No. 09/593,675, filed Jun. 14, 2000, now U.S. Pat. No. 6,406,777, and entitled A METAL AND GLASS STRUCTURE FOR USE IN SURFACE ENHANCED RAMAN SPECTROSCOPY AND METHOD FOR FABRICATING SAME.

BACKGROUND OF THE INVENTION

The present invention generally relates to the field of Raman spectroscopy, and more particularly, to a sensor for detecting chemicals both in gas and liquid environments using surface enhanced Raman spectroscopy.

Raman spectroscopy is an emission technique that involves inelastic scattering of incident laser energy and results in spectral peaks that are frequency shifted from the incident energy. The Raman bands arise from changes in polarizability in a molecule during vibration. As a result, virtually all organic molecules display a characteristic Raman emission. Therefore, a Raman sensor would not be limited to a specific class of molecules as is the case for the laser induced fluorescence (LIF) sensor. Raman spectrometry allows the fingerprinting of species present and is structurally specific. The inherently high resolution of Raman spectra often permits the analysis of several components in a mixture simultaneously.

The advent of inexpensive, portable Raman spectrometers has seen renewed interest in the area of Raman spectrometry. This new generation of spectrometers employs fiber-optic probes, holographic notch filters for rejection of the Rayleigh line, a single grating monochromator, and a charge-coupled device (CCD) detector for multichannel detection. These spectrometers contain a minimum of optical components as compared to conventional Raman instrumentation resulting in high throughputs; and, once coupled to a laser and spectrometer, optical-fiber probes require no further alignment.

Despite the advantages of Raman spectroscopy over other spectroscopic techniques and the technological advances in the area of Raman spectrometry, Raman spectroscopy is, inherently, an insensitive technique. To achieve detection limits in the low ppm range would require either the use of a multiple pass cell or long acquisition times. In the 1970s, it was discovered that Raman scattering from molecules adsorbed on such noble metals as silver, copper, and gold can be enhanced by as much as $10^6$ to $10^7$. This phenomenon, called surface enhanced Raman spectroscopy (SERS), is still not understood despite intensive theoretical and experimental research. It is believed that more than one mechanism is involved in the SERS phenomenon. Initially, the SERS technique was used as a means to probe adsorption at metal interfaces both in electrochemical and gas-phase environments. This technique has proven useful in deducing the effects of interfacial structure and reactivity on the adsorption process. However, the sensitivity of the technique as well as its exceptional spectral selectivity has made SERS attractive for a broad range of analytical applications. SERS can be used for trace organic analysis and as a detection method in gas chromatography, liquid chromatography, and thin layer chromatography. Electrochemical SERS and SERS of chemically modified surfaces have been used to detect aromatic compounds and chlorinated hydrocarbons, organic contaminants of environmental concern, in the ppm concentration range.

There are many applications in which detection of particular chemical species or analytes is desirable, as for example, hydrocarbons that may be present in ground water, toxic vapors in industrial environments, explosives, metal ions, narcotics, toxic anions, and chemical warfare agents.

However, a problem with optical fiber based SERS systems is that the optical excitation signal, and Raman emissions received by the collection optics can generate secondary Raman emissions in the optical fibers. Therefore, a need exists for an optical fiber based SERS sensor for detecting analytes of interest which is not affected by secondary Raman emissions within the excitation and collection fibers. A further need exists for an optical fiber based SERS sensor that may be deployed in physically challenging environments, such as at sea and in terrestrial bore holes.

SUMMARY OF THE INVENTION

The present invention provides a sensor for performing surface enhanced Raman spectroscopy (SERS) that includes a sensor body having a throughbore; a window mounted to the sensor body that is coterminous with the throughbore; a surface enhanced Raman scattering structure mounted to the window; an optical energy source for generating an optical excitation signal; a first optical fiber mounted in the throughbore for directing the optical excitation signal through the surface enhanced Raman scattering (SERS) structure; a second optical fiber mounted in the throughbore for receiving primary Raman emissions generated when an analyte in contact with the surface enhanced Raman scattering structure is irradiated by the optical excitation signal; and an optical detector for generating an optical signal representing the primary Raman emissions. A long pass filter is optically spliced in series with each second optical fiber for filtering out optical signals having wavelengths that are less than a predetermined wavelength. The sensor also includes a bandpass filter optically spliced to the first optical fiber for attenuating any secondary Raman emissions that may be stimulated in the first optical fiber by the optical excitation signal. A first lens collimates the excitation signal from the first optical fiber and another lens focuses the excitation signal onto the external surface of the SERS structure, i.e., at a SERS surface/liquid interface or SERS surface/gas interface when the sensor is being utilized. The sensor may further include electrodes for polarizing the SERS surface to attract analytes to the surface. The sensor may further include a liquid detector for determining when the sensor body is in contact with a liquid. Another embodiment of the invention includes electrodes in the vicinity of the SERS structure for performing electrochemical SERS.

The surface enhanced Raman scattering structure includes: a glass substrate having a roughened surface; an adhesion layer formed on the roughened surface; metal islands formed on the adhesion layer that define a metal patterned structure; and a self-assembled monolayer formed over the metal islands.

The sensor eliminates background interferences arising from fiber emissions, operates at long lengths of fiber (30+ meters), is able to do multiple samplings, is easily deployable, and withstands the shock and vibration associated with deployment in subsurface environments. The sensor may be used to detect subsurface pollutants of environmental concern, in particular BTEX, chlorinated hydrocarbons, anionic nutrients, metal ions, narcotics, explosive materials, and agents of chemical warfare.

These and other advantages of the invention will become more apparent upon review of the accompanying drawings and specification, including the claims.

BRIEF DESCRIPTION OF THE DRAWINGS

Throughout the several view, like elements are referenced using like references.

DESCRIPTION OF THE PREFERRED EMBODIMENT

Figure 1:
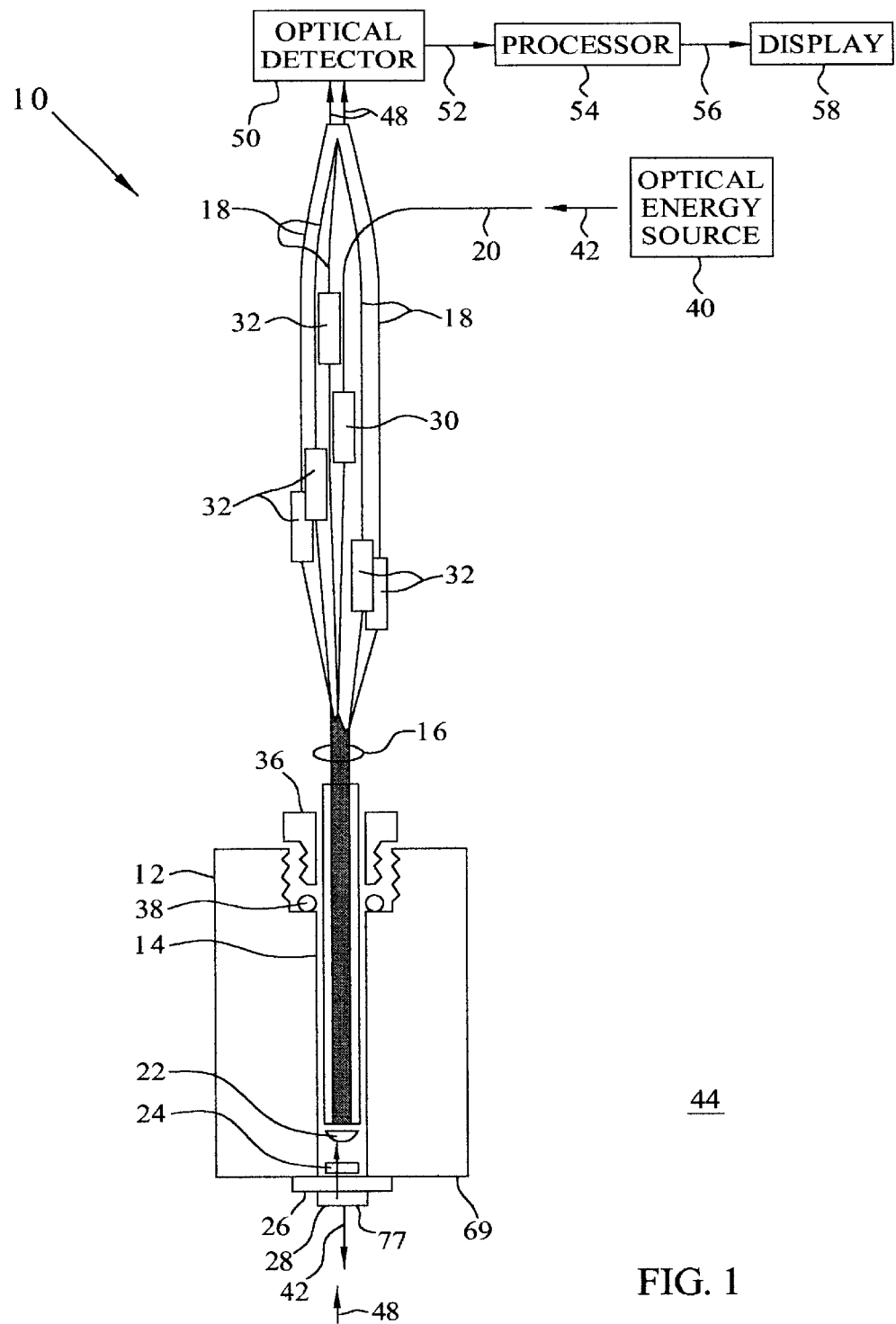
FIG. 1 illustrates a first embodiment of a fiber optic sensor for performing surface enhanced Raman spectroscopy that includes a SERS structure mounted to the window of the sensor.

Referring to FIG. 1, the present invention is directed to a sensor 10 for performing surface enhanced Raman spectroscopy. The sensor 10 includes a sensor body 12 having a throughbore 14 in which is positioned a fiber optic bundle 16 comprised of collection optical fibers 18, excitation optical fiber 20, collimating lens 22, focusing lens 24, window 26, and a Surface Enhanced Raman Spectroscopy (SERS) structure 28 that is described in commonly assigned U.S. patent application Ser. No. 09/593,675, filed Jun. 14, 2000, now U.S. Pat. No. 6,406,777, and entitled A METAL AND GLASS STRUCTURE FOR USE IN SURFACE ENHANCED RAMAN SPECTROSCOPY AND METHOD FOR FABRICATING SAME, incorporated herein by reference. Filter 30 is optically aligned and spliced to excitation optical fiber 20; and a filter 32 is optically aligned and spliced to each of collection optical fibers 18. Bushing 36 is threaded into sensor body 12 to secure the fiber optic bundle 16 within the bore 14 of the sensor body 12. An O-ring 38 may be interposed between bushing 36 and sensor body 12 to provide a watertight seal therebetween. Window 26 on which SERS structure 28 is bonded may be secured to sensor body 12 using adhesives, not shown, or by mechanical means, such as flanges or clamps.

In the operation of sensor 10, optical energy source 40 emits a light signal 42 that is directed to propagate through excitation optical fiber 20. Optical energy source 40 may be implemented as a krypton ion laser, near infrared (IR) diode laser, or Nd:YAG laser that generates light signals having wavelengths in the range, by way of example, from 647 to 1064 nm. Optical filter 30 is a bandpass filter that removes Raman emissions that may be excited within excitation optical fiber 20 by light signal 42. Light signal 42 is emitted from the polished end of excitation optical fiber 20 and then is collimated by lens 22 and focused by lens 24 onto the external surface 77 of the SERS structure 28, which is a SERS surface/liquid or SERS surface/vapor interface when sensor 10 is being utilized. Next, focused and collimated light signal 42 passes through window 26 and SERS structure 28 and is then emitted from sensor body 12 through the SERS structure 28 into the environment 44, which for example, may be a liquid or gas in which an analyte of interest may be present.

If an analyte of interest is present in environment 44, then the interaction of light signal 42 and the analyte in the presence of SERS structure 28 stimulates the generation of primary Raman emissions 48 that are transmitted through window 26, focusing lens 24, and collimating lens 22, and then enter collection optical fibers 18. Primary Raman emissions 48 are directed by collection optical fibers 18 through long pass filters 32 which block the Rayleigh line, thereby preventing excitation of secondary Raman emissions in collection optical fibers 18. The primary Raman emissions 48 are directed to optical detector 50 which detects the spectral components of signals 48. Secondary Raman emissions are generally defined as Raman emissions that are not stimulated by irradiation of the analyte by optical excitation signal 42. Optical detector 50 generates signal 52 that represents the primary Raman emissions 48, particularly, the spectral components of primary Raman signals 48. In response to receiving signal 52, processor 54 determines the identity of the analyte that resulted in the generation of primary Raman emissions 48, as for example, by comparing the value of signal 52 to values stored in a look-up table implemented in processor 54. If the value of signal 52 falls within a predetermined difference between the value of signal 52 and a reference value stored in the look-up table, then the processor 54 generates an output signal 56 that causes display 58 to present the identity the detected analyte, i.e., particular chemical associated with the reference value. The look-up table may include reference values for many chemical species of interest, thereby providing sensor 10 with the capability for identifying a host of chemical species that may cause SERS structure 28 to stimulate primary Raman emissions 48.

Figure 2:
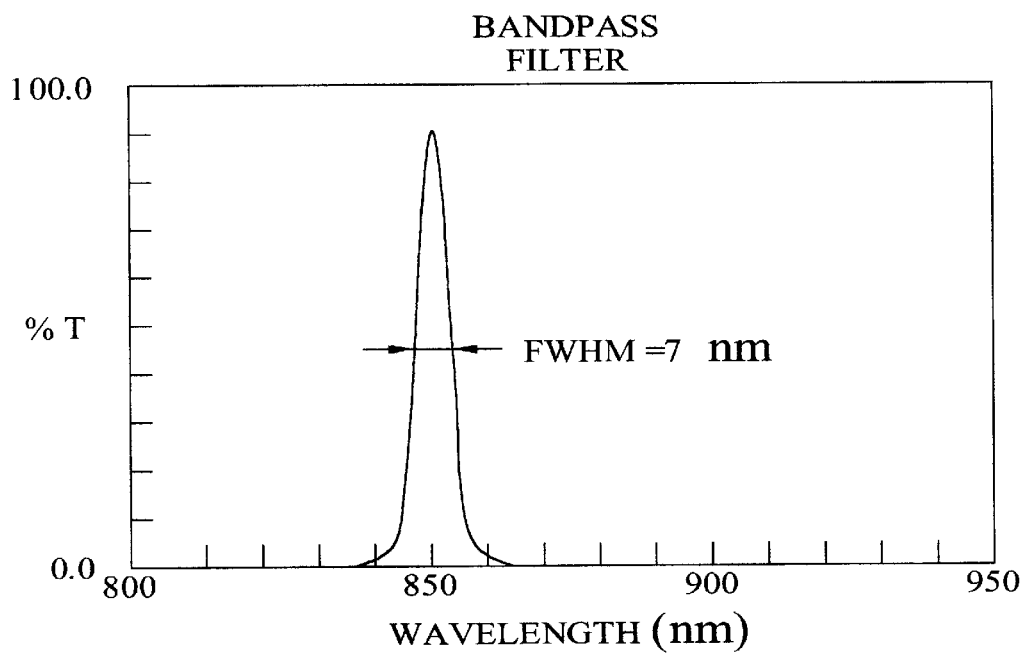
FIG. 2 shows transmission curves for the bandpass filter of FIG. 1 operating when the excitation light signal has a wavelength of 852 nm.
Figure 3:
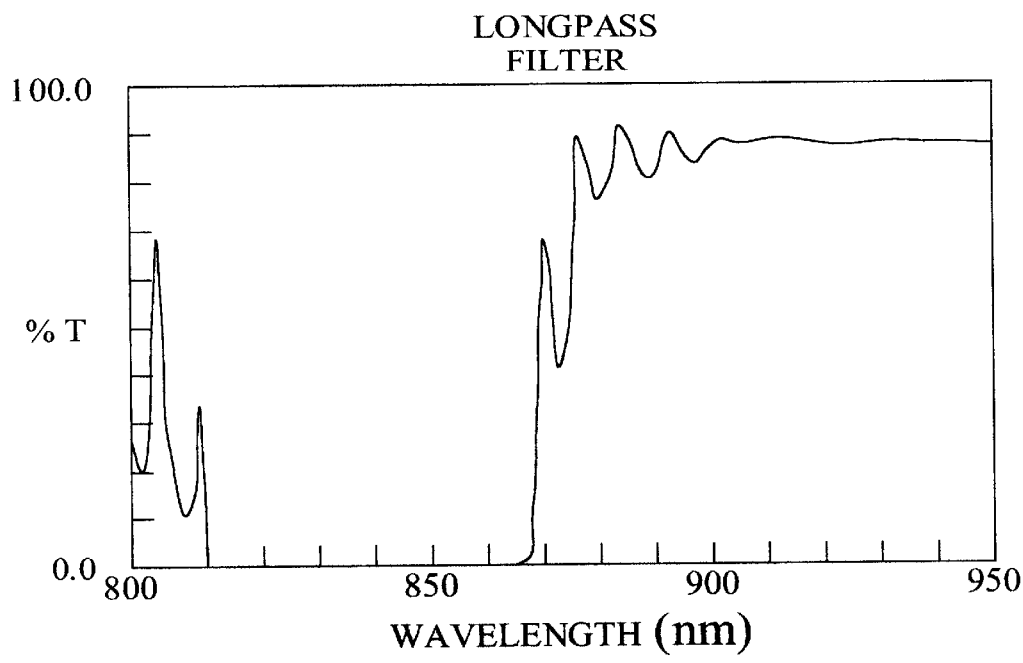
FIG. 3 shows transmission curves for the long pass filter of FIG. 1 operating when the excitation light signal has a wavelength of 852 nm.

By way of example, collection optical fibers 18 and 20, and filters 30 and 32 are available as a commercial package from Visionex, Inc., and may be selected for specific excitation wavelengths. FIGS. 2 and 3 shows transmission curves for the bandpass filter 30 and long pass filters 32, respectively, operating when excitation light signal 42 has a wavelength of 852 nm. FIG. 2 shows that the bandpass filter 30 has a very narrow bandpass centered about 850 nm and a full width, half maximum of value of 7 nm. FIG. 3 shows that the long pass filter 32 sharply passes light having wavelengths of about 868 nm or higher, but sharply attenuates light having shorter wavelengths than that.

Figure 4:
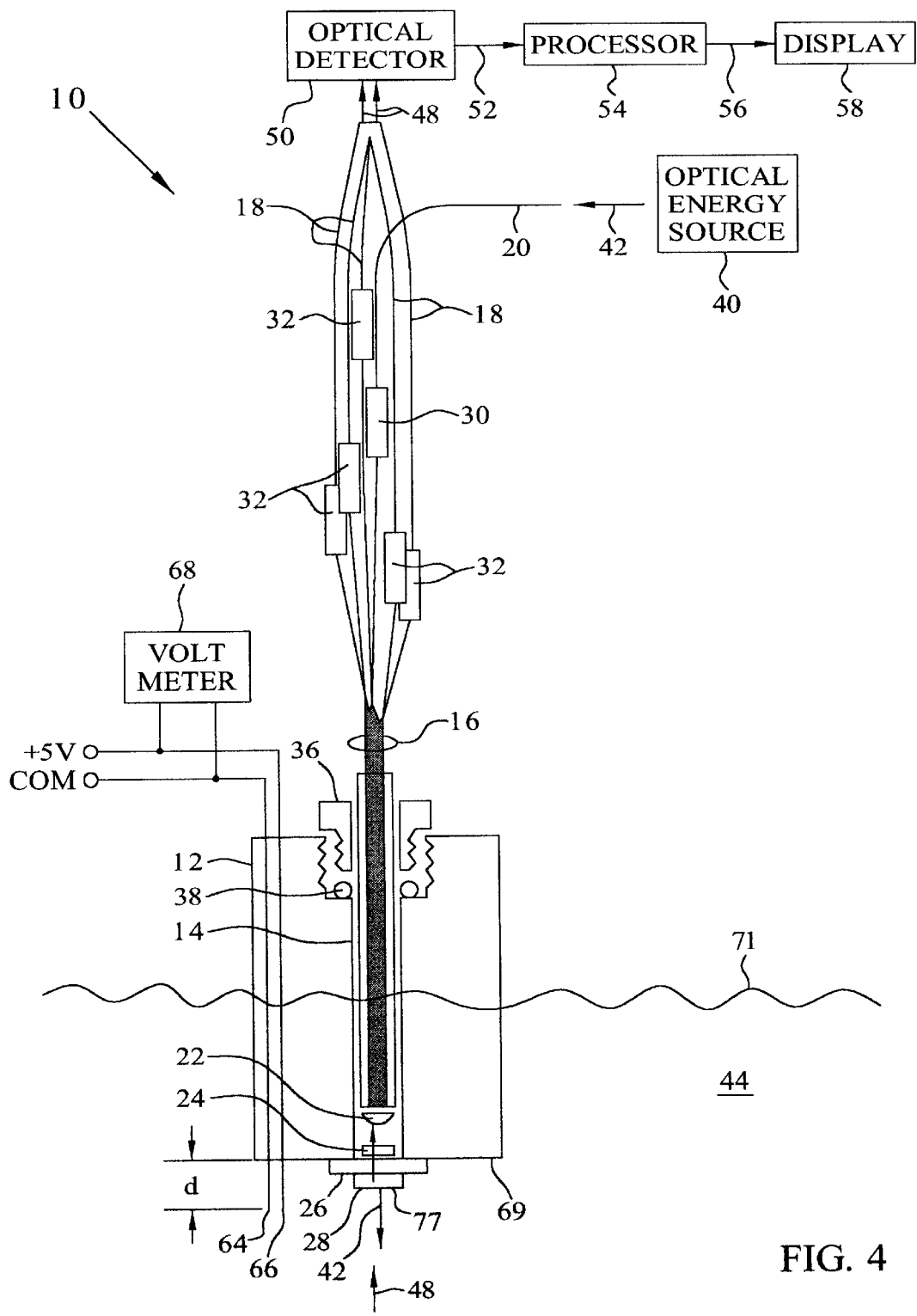
FIG. 4 illustrates a second embodiment fiber optic sensor for performing surface enhanced Raman spectroscopy that further includes a liquid level detector.

Referring to FIG. 4, the sensor may further include a liquid detector comprised of wire leads 60 and 62, each having for example, a 0.5 mm diameter, and a volt meter 68. The wire leads 60 and 62 each may be mounted through with bores, not shown, in sensor body 12 and secured to the sensor body with epoxy. The ends 64 and 66 of wire leads 60 and 62, respectively, extend a distance d beneath the optical output end of the sensor body. The distance d may typically be in the range of 1 to 3 mm. Wire leads 60 and 62 are connected, for example, to a +5 V power supply, not shown, and are preferably made of platinum or platinum alloys to provide the leads with excellent chemical resistance. In general, voltmeter 68 will read approximately +5 V if the optical output and detection end 69 of sensor body 12 is not immersed in a liquid. However, if optical output and detection end 69 of sensor body 12 is immersed in a liquid 71, the voltmeter 68 will display a reading of about 0 V, because any conductivity of liquid 71 will cause a short circuit between wire leads 60 and 62. The liquid sensor is important because it provides a means by which one may determine whether the sensor body 12 comes into contact with a liquid environment, as for example, in applications where sensor body 12 is lowered into bore holes, tubes, and the like.

Figure 5:
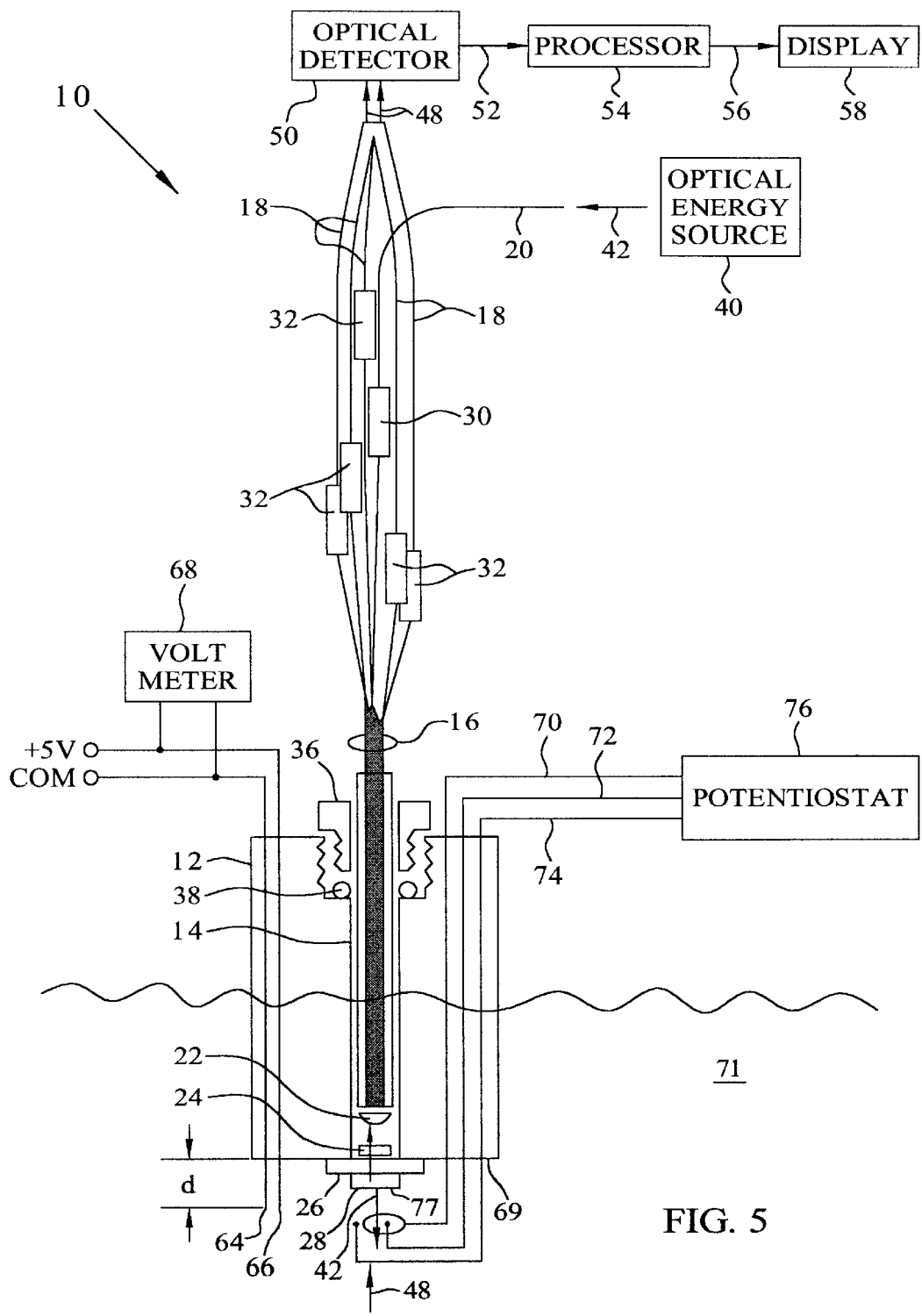
FIG. 5 illustrates a third embodiment of a fiber optic sensor for performing surface enhanced Raman spectroscopy that includes electrodes for performing electrochemical SERS.

Referring to FIG. 5, sensor 10 may be employed to perform electrochemical SERS and includes counter electrode 70, working electrode 72, reference electrode 74, and potentiostat 76. Counter electrode 70 is preferably made of platinum or platinum alloys because platinum has excellent chemical resistance. However, the embodiment of sensor 10 shown in FIG. 5 does not include a SERS structure 28. Working electrode 72 is preferably made of silver, gold, or copper since those materials exhibit excellent SERS enhancement, i.e., they show a SERS effect when roughened. Reference electrode 74 preferably is made of silver coated with silver chloride. Electrodes 70, 72, and 74 may be implemented as wires, where electrodes 70 and 74 have a 0.5 mm diameter and electrode 72 has a 2 mm diameter. The electrodes 70, 72, and 74 are fitted through bores, not shown, in the sensor body 12 and may be secured with epoxy. In electrochemical SERS, adsorption of analytes of interest onto the working electrode 70 is induced by varying the potential of working electrode 72, as for example, between +2.2 and −2.2 volts. The surface of working electrode 72 may be roughened in-situ in the presence of the analyte by performing repeated oxidation/reduction cycles (ORCs). The ORCs are performed by allowing the potentiostat to cycle the working electrode 72 between +0.2 and −0.3 volts, vs. the reference electrode 74 for approximately 10 minutes at a scan rate of 0.2 V/s. Since the adsorption isotherm of an analyte on an electrode surface is potential dependent, controlling the applied potential to working electrode 72 offers some degree of selectivity as to the types of analytes that may be detected. Example of analytes that may be detected using electrodes 70, 72, and 74 of sensor 10 to perform electrochemical SERS include, but are not limited to naphthalene, toluene, and benzene.

Figure 6:
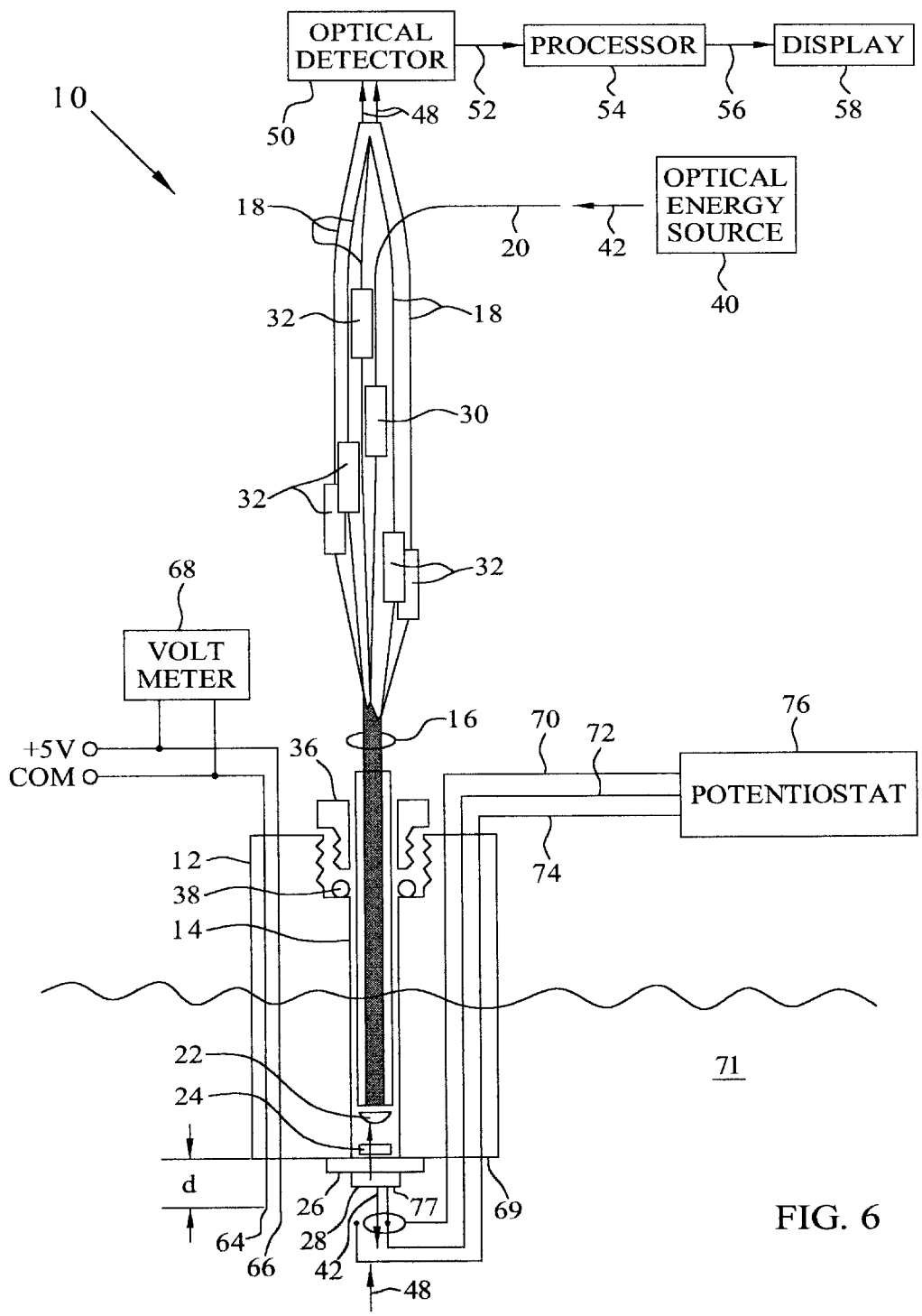
FIG. 6 illustrates a third embodiment of a fiber optic sensor for performing surface enhanced Raman spectroscopy that includes electrodes for performing SERS, where one of the electrodes is in ohmic contact with the SERS structure.

FIG. 6 illustrates another embodiment of sensor 10 wherein working electrode 72 is 18 placed in ohmic contact with the external surface 77 of SERS structure 28, preferably using 19 mechanical fastening means, such as clamps, not shown, so that a potential may be applied to the 20 surface 77 in order to attract ions from the analyte of interest and thus, increase the sensitivity of sensor 10. Mechanical fastening means are preferred over an electrically conductive epoxy because epoxy may generate its own Raman emissions if excited by light signal 42 that could contaminate Raman emissions 48.

We claim:

1. A sensor for performing surface enhanced Raman spectroscopy, comprising:
    a sensor body having a throughbore;
    a window mounted to said sensor body that is coterminous with said throughbore;
    a surface enhanced Raman scattering structure that is mounted to said window and includes:
        a glass substrate having a roughened surface;
        an adhesion layer formed on said roughened surface;
        metal islands formed on said adhesion layer that define a metal patterned structure; and
        a self-assembled monolayer formed over said metal islands;
    an optical energy source for generating an optical excitation signal;
    a first optical fiber mounted in said throughbore for directing said optical excitation signal through
    said surface enhanced Raman scattering structure;
    a second optical fiber mounted in said throughbore for receiving primary Raman emissions generated when an analyte in contact with said surface enhanced Raman scattering structure is irradiated by said optical excitation signal; and
    an optical detector for generating an optical signal representing said primary Raman emissions.

2. The sensor of claim 1 which further includes a bandpass filter for attenuating any secondary Raman emissions stimulated by said optical excitation signal in said first optical fiber.

3. The sensor of claim 1 further including a long pass filter for filtering optical signals having wavelengths less than a predetermined wavelength.

4. The sensor of claim 2 further including a processor for identifying said analyte in response to receiving said output signal generated by said optical detector.

5. The sensor of claim 3 wherein said processor generates a signal representing said analyte and further including a display for presenting human readable indicia representing said analyte.

6. The sensor of claim 1 further including a liquid sensor having:
    a voltage detecting device;
    a first lead wire that extends from said sensor body and is electrically connected to said voltage detecting device; and
    a second lead wire that extends from said sensor body and is electrically connected to said voltage detecting device.

7. The sensor of claim 1 further including:
    a potentiostat;
    a working electrode that extends through said sensor body, is electrically connected to said potentiostat, and is in ohmic contact with said surface enhanced Raman structure;
    a counter electrode that extends through said sensor body and is electrically connected to said potentiostat; and
    a reference electrode that extends through said sensor body and is electrically connected to said potentiostat.

8. The sensor of claim 1 further including a first lens for focusing said light signal emitted by said optical energy source.

9. The sensor of claim 1 further including a second lens for collimating said light signal emitted by said optical energy source.

10. A sensor for performing surface enhanced Raman spectroscopy, comprising:
    a sensor body having a throughbore;
    a window mounted to said sensor body that is coterminous with said throughbore;
    an optical energy source for generating an optical excitation signal;
    a surface enhanced Raman scattering structure that is mounted to said window and includes:
        a glass substrate having a roughened surface;
        an adhesion layer formed on said roughened surface;

metal islands formed on said adhesion layer; and a self-assembled monolayer formed over said metal islands;

a first optical fiber mounted in said throughbore for directing said optical excitation signal through said surface enhanced Raman scattering structure;

a second optical fiber mounted in said throughbore for receiving primary Raman emissions generated when an analyte in contact with said surface enhanced Raman scattering structure is irradiated by said optical excitation signal;

an optical detector for generating an optical signal representing said primary Raman emissions; a potentiostat;

a working electrode that extends through said sensor body and is electrically connected to said potentiostat and to said metal islands;

a counter electrode that extends through said sensor body and is electrically connected to said potentiostat; and a reference electrode that extends through said sensor body and is electrically connected to said potentiostat.

11. The sensor of claim 10 further including a liquid sensor having:

a voltage detecting device;

a first lead wire that extends from said sensor body and is electrically connected to said voltage detecting device; and a second lead wire that extends from said sensor body and is electrically connected to said voltage detecting device.

12. The sensor of claim 10 further including a processor for identifying said analyte in response to receiving said output signal generated by said optical detector.

13. The sensor of claim 12 wherein said processor generates a signal representing said analyte; and further including a display for presenting human readable indicia representing said analyte.

* * * * *